United States Patent
Masuda

(10) Patent No.: US 11,490,860 B2
(45) Date of Patent: Nov. 8, 2022

(54) BIOLOGICAL INFORMATION MONITORING SYSTEM, BED SYSTEM, AND BIOLOGICAL INFORMATION MONITORING METHOD

(71) Applicant: MINEBEA MITSUMI INC., Nagano (JP)

(72) Inventor: Shigemi Masuda, Fukuroi (JP)

(73) Assignee: MINEBEA MITSUMI Inc., Nagano (JP)

( * ) Notice: Subject to any disclaimer, the term of this patent is extended or adjusted under 35 U.S.C. 154(b) by 0 days.

(21) Appl. No.: 17/442,701

(22) PCT Filed: Apr. 3, 2020

(86) PCT No.: PCT/JP2020/015303
§ 371 (c)(1),
(2) Date: Sep. 24, 2021

(87) PCT Pub. No.: WO2020/213431
PCT Pub. Date: Oct. 22, 2020

(65) Prior Publication Data
US 2022/0142582 A1     May 12, 2022

(30) Foreign Application Priority Data

Apr. 15, 2019   (JP) .............................. JP2019-077369

(51) Int. Cl.
*A61B 5/00*     (2006.01)
*A61B 5/0205*   (2006.01)
(Continued)

(52) U.S. Cl.
CPC .......... *A61B 5/6892* (2013.01); *A61B 5/0205* (2013.01); *A61B 5/1102* (2013.01);
(Continued)

(58) Field of Classification Search
CPC ... A61B 5/6892; A61B 5/0205; A61B 5/1102; A61B 5/113; A61B 5/7278;
(Continued)

(56) References Cited

U.S. PATENT DOCUMENTS 4,738,264 A * 4/1988 Orlando ............... A61B 5/0002
                                                   600/534
5,796,340 A * 8/1998 Miller .................. A61B 5/0205
                                                   600/534

(Continued)

FOREIGN PATENT DOCUMENTS

CN       108289638 A      7/2018
CN       108289639 A      7/2018
(Continued)

OTHER PUBLICATIONS

English translation of the Written Opinion for corresponding International Application No. PCT/JP2020/015303 dated Jun. 23, 2020.

(Continued)

*Primary Examiner* — May A Abouelela
(74) *Attorney, Agent, or Firm* — Pearne & Gordon LLP

(57) ABSTRACT

A biological information monitoring system (100) configured to monitor biological information of a subject (S) on a bed (BD) includes at least one load detector (11, 12, 13, 14) provided below the bed or legs of the bed and configured to detect a load of the subject on the bed, a waveform calculation unit (31) configured to calculate a waveform indicating a temporal variation in a detected value of the at least one load detector in accordance with respiration or a heartbeat of the subject, and a biological information calculation unit (32) configured to calculate a respiration rate or a heart rate of the subject by using the waveform. The biological information calculation unit includes a first calculation unit (321) configured to calculate the respiration rate or the heart rate of the subject by a first means based on the waveform, a (Continued)

second calculation unit (322) configured to calculate the respiration rate or the heart rate of the subject by a second means that differs from the first means and includes normalizing the waveform, and a calculation control unit (320) configured to cause the second calculation unit to calculate the respiration rate or the heart rate when an amplitude of the waveform is a threshold value or less.

11 Claims, 9 Drawing Sheets

(51) Int. Cl.
  *A61B 5/11* (2006.01)
  *A61B 5/113* (2006.01)
  *G01G 19/44* (2006.01)
  *G01G 19/52* (2006.01)
(52) U.S. Cl.
  CPC ............ *A61B 5/113* (2013.01); *A61B 5/7278* (2013.01); *G01G 19/445* (2013.01); *G01G 19/52* (2013.01); *A61B 2562/0252* (2013.01); *A61B 2562/046* (2013.01)
(58) Field of Classification Search
  CPC ...... A61B 2562/0252; A61B 2562/046; A61B 5/1115; A61B 5/72; A61B 5/024; A61B 5/0816; A61B 5/6891; G01G 19/445; G01G 19/52; G01G 19/50
  USPC .......................................................... 600/484
  See application file for complete search history.

(56) References Cited

U.S. PATENT DOCUMENTS

| | | | | |
|---|---|---|---|---|
| 8,905,928 | B2* | 12/2014 | Hayes | A61B 5/6887 600/300 |
| 9,592,005 | B2* | 3/2017 | Oakhill | G16H 50/20 |
| 9,883,809 | B2* | 2/2018 | Klap | A61B 5/1116 |
| 10,898,085 | B2* | 1/2021 | De Groot | A61B 5/6892 |
| 2004/0010202 | A1* | 1/2004 | Nakatani | A61B 5/0816 600/529 |
| 2004/0254482 | A1* | 12/2004 | Anderson | A61B 5/02007 600/529 |
| 2008/0077020 | A1* | 3/2008 | Young | A61B 5/0022 73/726 |
| 2008/0167561 | A1* | 7/2008 | Ruotoistenmaki | G01L 1/2231 600/484 |
| 2008/0306351 | A1* | 12/2008 | Izumi | A61B 5/4815 600/300 |
| 2010/0094139 | A1* | 4/2010 | Brauers | A61B 5/6887 600/595 |
| 2011/0034811 | A1* | 2/2011 | Naujokat | A61B 5/113 600/484 |
| 2014/0005502 | A1* | 1/2014 | Klap | A61B 5/1116 600/300 |
| 2014/0257050 | A1 | 9/2014 | Kuroda et al. | |
| 2015/0045630 | A1* | 2/2015 | Poliakine-Baruchi | A61B 5/447 600/595 |
| 2015/0164438 | A1* | 6/2015 | Halperin | G16H 20/10 340/573.1 |
| 2018/0146889 | A1 | 5/2018 | Akatsu et al. | |
| 2018/0146917 | A1 | 5/2018 | Iida et al. | |
| 2018/0206793 | A1 | 7/2018 | Akatsu et al. | |
| 2019/0150843 | A1 | 5/2019 | Akatsu et al. | |
| 2019/0150844 | A1 | 5/2019 | Akatsu et al. | |
| 2019/0151174 | A1 | 5/2019 | Akatsu et al. | |
| 2019/0167202 | A1 | 6/2019 | Akatsu et al. | |
| 2019/0183382 | A1 | 6/2019 | Akatsu et al. | |
| 2019/0328320 | A1* | 10/2019 | Lim | A61B 5/4818 |
| 2019/0328332 | A1* | 10/2019 | Murai | A61B 5/0205 |
| 2020/0178887 | A1* | 6/2020 | Correa | A61B 5/1115 |
| 2020/0178892 | A1* | 6/2020 | Maslik | A61B 5/4836 |
| 2020/0367810 | A1* | 11/2020 | Shouldice | A61B 5/4812 |
| 2021/0106256 | A1* | 4/2021 | Kogure | A61B 5/107 |
| 2021/0128064 | A1* | 5/2021 | Ghassemi | A61B 5/308 |
| 2021/0153777 | A1 | 5/2021 | Masuda | |

FOREIGN PATENT DOCUMENTS

| | | |
|---|---|---|
| CN | 108289779 A | 7/2018 |
| CN | 109414223 A | 3/2019 |
| CN | 109414224 A | 3/2019 |
| CN | 109475322 A | 3/2019 |
| CN | 109475323 A | 3/2019 |
| CN | 109475324 A | 3/2019 |
| JP | S61-24010 B2 | 6/1986 |
| JP | 2007-283071 A | 11/2007 |
| JP | 4002905 B2 | 11/2007 |
| JP | 2010-284498 A | 12/2010 |
| JP | 4829020 B | 11/2011 |
| JP | 2014-171513 A | 9/2014 |
| JP | 2016-022276 A | 2/2016 |
| JP | 61-05703 B1 | 3/2017 |
| JP | 2017-064350 A | 4/2017 |
| JP | 2019-030363 A | 2/2019 |

OTHER PUBLICATIONS

International Search Report for corresponding International Application No. PCT/JP2020/015303 dated Jun. 23, 2020.
Written Opinion for corresponding International Application No. PCT/JP2020/015303 dated Jun. 23, 2020.
Notice of Reasons for Rejection dated Oct. 6, 2020 for corresponding Japanese Application No. 2019-077369 and English translation.
Notice of Reasons for Rejection dated Jan. 12, 2021 for corresponding Japanese Application No. 2019-077369 and English translation.
Chinese Office Action dated Feb. 18, 2022 for corresponding Chinese Application No. 202080028262.2 and English translation.

* cited by examiner (a)

(b)

BIOLOGICAL INFORMATION MONITORING SYSTEM, BED SYSTEM, AND BIOLOGICAL INFORMATION MONITORING METHOD

TECHNICAL FIELD

The present invention relates to a biological information monitoring system, a bed system, and a biological information monitoring method.

BACKGROUND ART

In the medical and long-term care fields, detecting the load of a subject on a bed via a load detector and acquiring biological information of the subject on the basis of the detected load has been proposed.

Patent Document 1 discloses calculating a respiration rate and a heart rate of a subject on the basis of a load signal from four load converters.

CITATION LIST

Patent Literature

Patent Document 1: JP 61-24010 B

SUMMARY OF INVENTION

Technical Problem

In the calculation of the biological information using the detected value of the load detector, various error factors intervene, and these error factors need to be eliminated to calculate the biological information more accurately.

An object of the present invention is to provide a biological information monitoring system, a bed system, and a biological information monitoring method capable of more accurately calculating biological information of a subject.

Solution to Problem

According to a first aspect of the present invention, provided is a biological information monitoring system configured to monitor biological information of a subject on a bed. The biological information monitoring system includes at least one load detector provided below the bed or legs of the bed and configured to detect a load of the subject on the bed, a waveform calculation unit configured to calculate a waveform indicating a temporal variation in a detected value of the at least one load detector in accordance with a respiration or a heartbeat of the subject, and a biological information calculation unit configured to calculate a respiration rate or a heart rate of the subject by using the waveform. The biological information calculation unit includes a first calculation unit configured to calculate the respiration rate or the heart rate of the subject by a first means based on the waveform, a second calculation unit configured to calculate the respiration rate or the heart rate of the subject by a second means that differs from the first means and includes normalizing the waveform, and a calculation control unit configured to cause the second calculation unit to calculate the respiration rate or the heart rate when an amplitude of the waveform is a threshold value or less.

In the biological information monitoring system according to the first aspect, the at least one load detector may be a plurality of load detectors, the waveform calculation unit may be configured to find a center of gravity position of the subject based on a detected value of each of the plurality of load detectors, and calculate a respiration waveform of the subject based on movement of the center of gravity position in accordance with the respiration of the subject, the first calculation unit may be configured to calculate the respiration rate of the subject by the first means based on the respiration waveform, the second calculation unit may be configured to calculate the respiration rate of the subject by the second means that includes normalizing the respiration waveform, and the calculation control unit may be configured to cause the second calculation unit to calculate the respiration rate when an amplitude of the respiration waveform is the threshold value or less.

In the biological information monitoring system of the first aspect, the first means may include detecting a peak of the waveform.

The biological information monitoring system according to the first aspect may further include a bed occupancy determination unit configured to determine whether or not the subject occupies the bed based on the respiration rate or the heart rate of the subject being calculated.

In the biological information monitoring system according to the first aspect, the waveform calculation unit may be configured to calculate the waveform indicating the temporal variation in the detected value of the at least one load detector in accordance with the respiration of the subject, and the waveform indicating the temporal variation in the detected value of the at least one load detector in accordance with the heartbeat of the subject, the first calculation unit may be configured to calculate the respiration rate of the subject by the first means based on the waveform indicating the temporal variation in accordance with the respiration, and calculate the heart rate of the subject by the first means based on the waveform indicating the temporal variation in accordance with the heartbeat, the second calculation unit may be configured to calculate the respiration rate of the subject by the second means that includes normalizing the waveform indicating the temporal variation in accordance with the respiration, and calculate the heart rate of the subject by the second means that includes normalizing the waveform indicating the temporal variation in accordance with the heartbeat, and the calculation control unit may be configured to cause the second calculation unit to calculate the respiration rate when an amplitude of the waveform indicating the temporal variation in accordance with the respiration is a first threshold value or less, and cause the second calculation unit to calculate the heart rate when an amplitude of the waveform indicating the temporal variation in accordance with the heartbeat is a second threshold value or less.

According to a second aspect of the present invention, provided is a bed system including a bed and the biological information monitoring system according to the first aspect.

According to a third aspect of the present invention, provided is a biological information monitoring method for monitoring biological information of a subject on a bed. The biological information monitoring method includes detecting a load of the subject on the bed by at least one load detector provided below the bed or legs of the bed, calculating a waveform indicating a temporal variation in a detected value of the at least one load detector in accordance with a respiration or a heartbeat of the subject, and calculating a respiration rate or a heart rate of the subject by using the waveform. The calculating a respiration rate or a heart rate of the subject includes calculating the respiration rate or the heart rate of the subject by a first means based on the waveform, calculating the respiration rate or the heart rate of the subject by a second means that differs from the first means and includes normalizing the waveform, and causing a second calculation unit to calculate the respiration rate or the heart rate when an amplitude of the waveform is a threshold value or less.

In the biological information monitoring method according to the third aspect, the at least one load detector may be a plurality of load detectors, the calculating a waveform may include finding a center of gravity position of the subject based on a detected value of each of the plurality of load detectors, and calculating a respiration waveform of the subject based on movement of the center of gravity position in accordance with the respiration of the subject, the calculating the respiration rate of the subject by a first means may include calculating the respiration rate of the subject by the first means based on the respiration waveform, the calculating the respiration rate of the subject by a second means may include calculating the respiration rate of the subject by the second means that includes normalizing the respiration waveform, and the causing the second calculation unit to calculate the respiration rate when an amplitude of the waveform is a threshold value or less may include causing the second calculation unit to calculate the respiration rate when an amplitude of the respiration waveform is the threshold value or less.

In the biological information monitoring method of the third aspect, the first means may include detecting a peak of the waveform.

The biological information monitoring method according to the third aspect may further include determining whether or not the subject occupies the bed based on the respiration rate or the heart rate of the subject being calculated.

In the biological information monitoring method according to the third aspect, the calculating a waveform indicating a temporal variation in a detected value of the at least one load detector in accordance with a respiration or a heartbeat of the subject may include calculating the waveform indicating the temporal variation in the detected value of the at least one load detector in accordance with the respiration of the subject, and may further include calculating the waveform indicating the temporal variation in the detected value of the at least one load detector in accordance with the heartbeat of the subject, and the calculating a respiration rate or a heart rate of the subject by using the waveform may include calculating the respiration rate of the subject by using the waveform indicating the temporal variation in the detected value of the at least one load detector in accordance with the respiration of the subject, and may further include calculating the heart rate of the subject by using the waveform indicating the temporal change in the detected value of the at least one detector in accordance with the heartbeat of the subject. The calculating a respiration rate and a heart rate of the subject may include calculating the respiration rate of the subject by the first means based on the waveform indicating the temporal variation in accordance with the respiration of the subject, calculating the heart rate of the subject by the first means based on the waveform indicating the temporal variation in accordance with the heartbeat of the subject, calculating the respiration rate of the subject by the second means that includes normalizing the waveform indicating the temporal variation in accordance with the respiration of the subject, calculating the heart rate of the subject by the second means that includes normalizing the waveform indicating the temporal variation in accordance with the heartbeat of the subject, causing the second calculation unit to calculate the respiration rate when an amplitude of the waveform indicating the temporal variation in accordance with the respiration of the subject is a first threshold value or less, and causing the second calculation unit to calculate the heart rate when an amplitude of the waveform indicating the temporal variation in accordance with the heartbeat of the subject is a second threshold value or less.

Advantageous Effects of Invention

According to the biological information monitoring system of the present invention, biological information of a subject can be calculated more accurately.

DESCRIPTION OF EMBODIMENTS

Embodiments

A case in which a biological information monitoring system 100 (FIG. 1) according to an embodiment of the present invention is used in conjunction with a bed BD (FIG. 2) to calculate (estimate) a respiration rate of a subject S on the bed BD will now be described.

Figure 1:
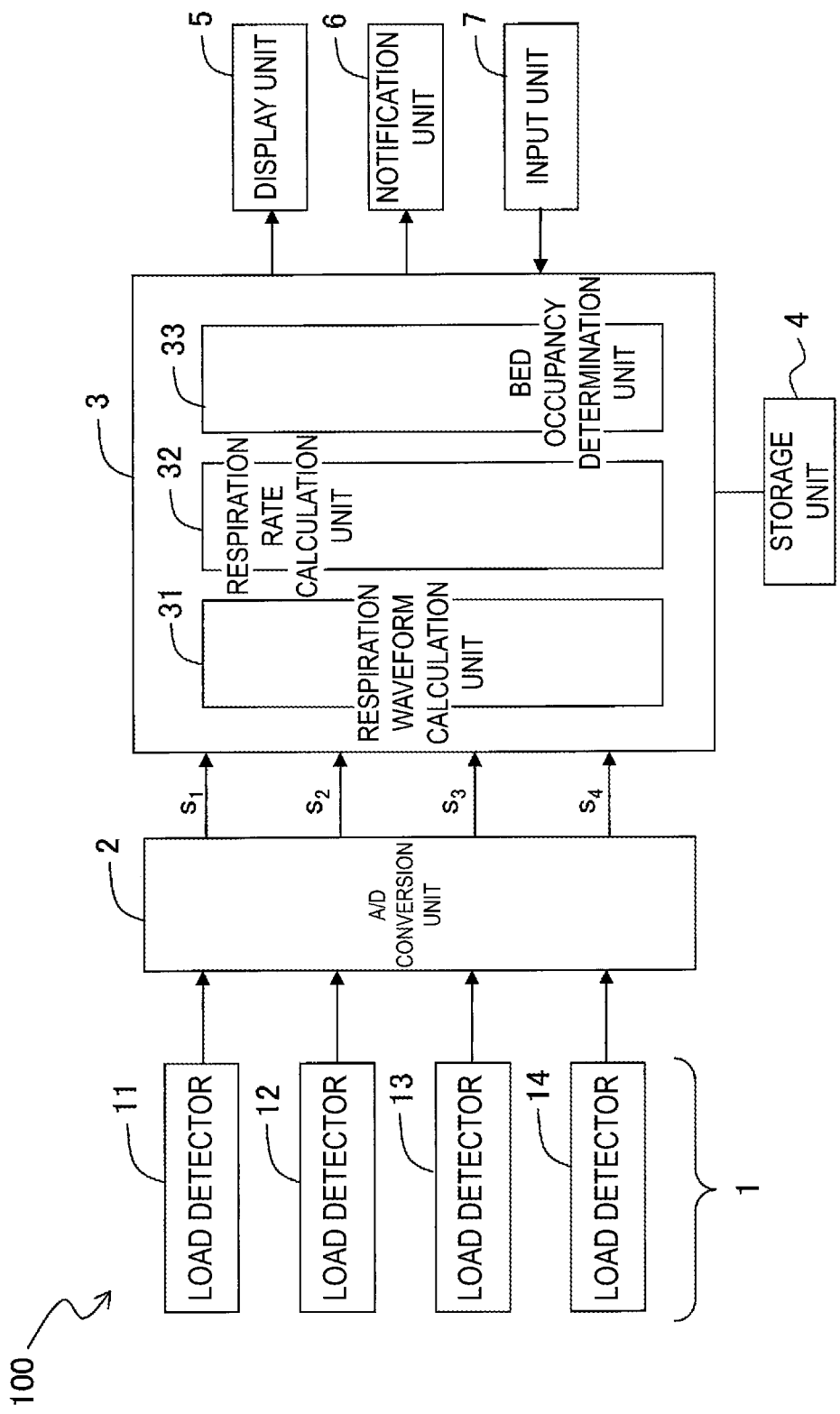
FIG. 1 is a block diagram illustrating a configuration of a biological information monitoring system according to an embodiment of the present invention.

As illustrated in FIG. 1, the biological information monitoring system 100 of this embodiment primarily includes a load detection unit 1, a control unit 3, and a storage unit 4. The load detection unit 1 and the control unit 3 are connected via an A/D conversion unit 2. A display unit 5, a notification unit 6, and an input unit 7 are further connected to the control unit 3.

The load detection unit 1 includes four load detectors 11, 12, 13, 14. Each of the load detectors 11, 12, 13, 14 is a load detector configured to detect a load using, for example, a beam type load cell. Such a load detector is described in JP 4829020 B and JP 4002905 B, for example. Each of the load detectors 11, 12, 13, 14 is connected to the A/D conversion unit 2 by wiring or wirelessly.

Figure 2:
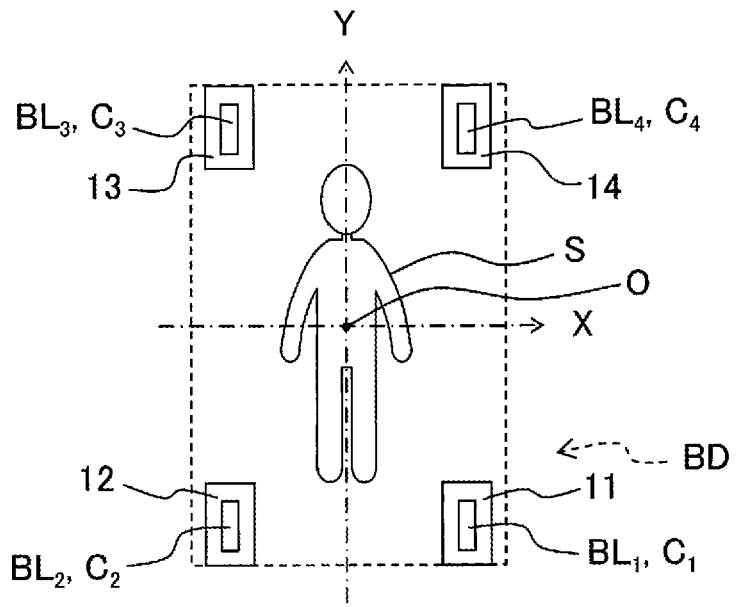
FIG. 2 is an explanatory view illustrating an arrangement of load detectors on a bed.

As illustrated in FIG. 2, the four load detectors 11 to 14 of the load detection unit 1 are respectively disposed below casters $C_1$, $C_2$, $C_3$, $C_4$ attached to lower ends of legs $BL_1$, $BL_2$, $BL_3$, $BL_4$ of the four corners of the bed BD used by the subject S.

The A/D conversion unit 2 includes an A/D converter configured to convert an analog signal from the load detection unit 1 into a digital signal, and is connected to the load detection unit 1 and the control unit 3 by wiring or wirelessly.

The control unit 3 is a dedicated or general-purpose computer, and a respiration waveform calculation unit 31, a respiration rate calculation unit (biological information calculation unit) 32, and a bed occupancy determination unit 33 are built into an interior of the control unit 3.

The storage unit 4 is a storage device configured to store data used in the biological information monitoring system 100, and a hard disk (magnetic disk), for example, can be used.

The display unit 5 is a monitor, such as a liquid crystal monitor, configured to display information output from the control unit 3 to a user of the biological information monitoring system 100.

The notification unit 6 includes a device, such as a speaker, configured to audibly provide a predetermined notification on the basis of information from the control unit 3.

The input unit 7 is an interface for performing a predetermined input to the control unit 3, and may be a keyboard and a mouse.

An operation of monitoring biological information (respiration rate and in-bed/out-of-bed) of the subject on the bed using such a biological information monitoring system 100 will now be described.

Figure 3:
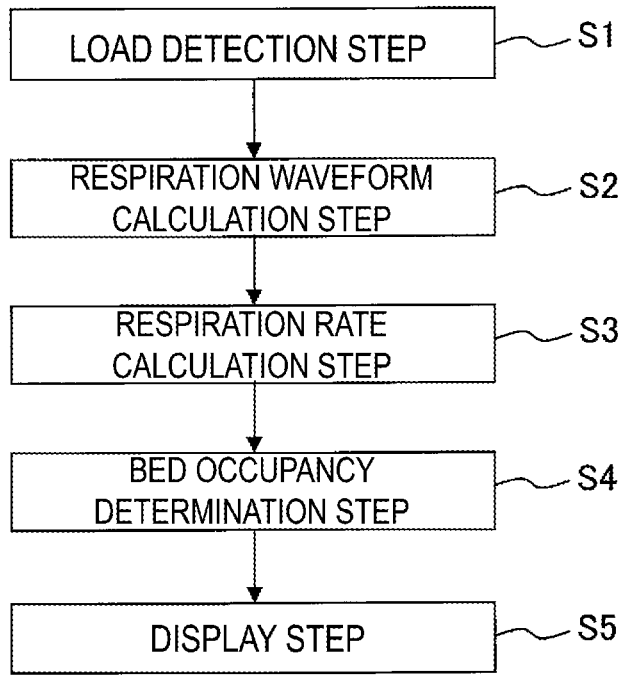
FIG. 3 is a flowchart indicating a method for monitoring biological information using the biological information monitoring system.

As illustrated in the flowchart of FIG. 3, the monitoring of the biological information of the subject using the biological information monitoring system 100 includes a load detection step S1 of detecting a load of the subject, a respiration waveform calculation step S2 of calculating a respiration waveform on the basis of the detected load (load value), a respiration rate calculation step S3 of calculating a respiration rate of the subject on the basis of the respiration waveform, a bed occupancy determination step S4 of determining whether the subject occupies the bed (in-bed/out-of-bed determination), and a display step S5 of displaying the respiration rate calculated in the respiration rate calculation step S3 and the determination result of the bed occupancy determination step S4.

Load Detection Step

In the load detection step S1, the load detectors 11, 12, 13, 14 are used to detect the load of the subject S on the bed BD. The load of the subject S on the bed BD is dispersedly applied to and dispersedly detected by the load detectors 11 to 14 disposed below the legs $BL_1$ to $BL_4$ at the four corners of the bed BD.

The load detectors 11 to 14 each detect a load (load change) and output the load as an analog signal to the A/D conversion unit 2. The A/D conversion unit 2 converts the analog signal into a digital signal with a sampling period of, for example, 5 milliseconds, and outputs the digital signal (hereinafter, referred to as a "load signal") to the control unit 3. Hereinafter, the load signals obtained by digitally converting, in the A/D conversion unit 2, the analog signals output from the load detectors 11, 12, 13, 14 are referred to as load signals $s_1$, $s_2$, $s_3$, $s_4$, respectively.

Respiration Waveform Calculation Step

In the respiration waveform calculation step S2, the respiration waveform calculation unit 31 calculates the respiration waveform of the subject S on the basis of the load signals $s_1$ to $s_4$ Human respiration is performed by moving the thorax and the diaphragm to expand and contract the lung. Here, at the time of inhalation, that is, when the lungs expand, the diaphragm moves downward and the internal organs also move downward. On the other hand, at the time of exhalation, that is, when the lungs contract, the diaphragm moves upward and the internal organs also move upward. As described in the specification of JP 6105703 B granted to the applicant of the present invention, the center of gravity of a person moves slightly when the internal organs move, and the direction of this movement is substantially an extending direction (body axial direction) of the spine.

In the present invention and the present specification, the term "respiration waveform" refers to a waveform indicating, on a time axis, a state of oscillation of the center of gravity of the subject oscillating in the body axial direction of the subject in accordance with the respiration of the subject. One cycle of the respiration waveform corresponds to one breath (exhalation and inhalation) of the subject. An amplitude of the respiration waveform is affected by the physique and depth of breathing of the subject. Specifically, for example, when the subject is lame or the subject takes a deep breath, the amplitude increases, and when the subject is small or the subject takes a shallow breath, the amplitude decreases.

The respiration waveform calculation unit 31 calculates the respiration waveform according to the following procedure.

Figure 4:
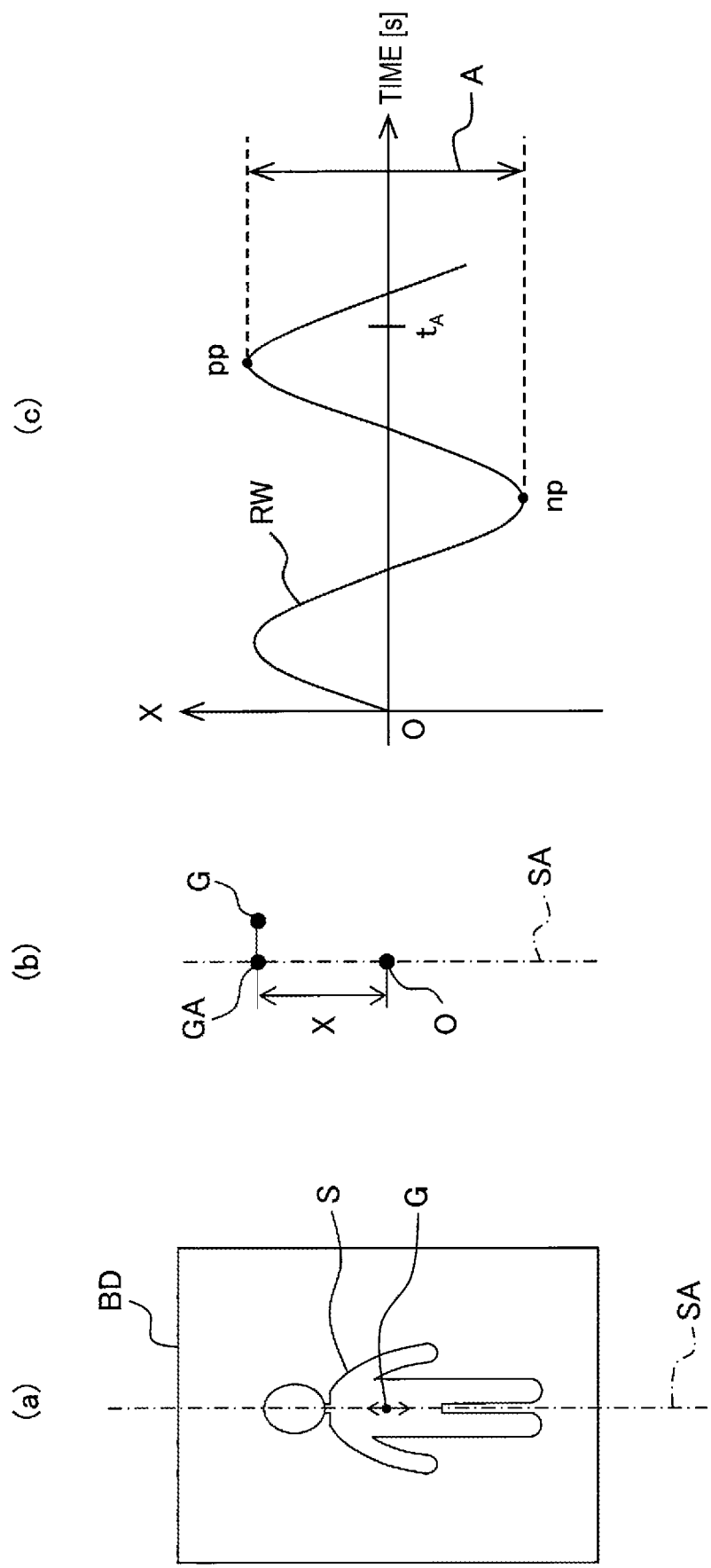
FIG. 4A is an explanatory view conceptually illustrating center of gravity of a subject oscillating in a body axial direction in response to respiration of the subject.
FIG. 4B is an explanatory view for describing a method of calculating a respiration waveform on the basis of oscillation of the center of gravity in accordance with the respiration of the subject.
FIG. 4C is a diagram illustrating an example of the respiration waveform drawn on the basis of the oscillation of the center of gravity in accordance with the respiration of the subject.

First, the respiration waveform calculation unit 31 calculates a position of a center of gravity G of the subject S at individual sampling times on the basis of the load signals $s_1$ to $s_4$ from the load detection unit 1. As illustrated in FIG. 4A, the center of gravity G of the subject S oscillates substantially in the direction of a body axis SA of the subject S in response to the respiration of the subject S.

Next, as illustrated in FIG. 4B, the respiration waveform calculation unit 31 projects the calculated position of the center of gravity G of each of the sampling times onto the body axis SA to find a position GA, and calculates a distance X between an oscillation center O of the oscillation of the center of gravity G corresponding to the respiration and the position GA. With the calculated distance X at each sampling time successively plotted with the horizontal axis as the time axis, a respiration waveform RW illustrated in FIG. 4C is acquired. Note that, instead of the distance X, a linear distance X' between the center of gravity G and the oscillation center O may be used.

The respiration waveform calculation unit 31 calculates the distance X at each sampling time as data indicating the respiration waveform RW, and outputs the data to the respiration rate calculation unit 32. Further, the respiration waveform calculation unit 31 may output data indicating the respiration waveform RW to a respiration waveform drawing unit (not illustrated). In this case, the respiration waveform drawing unit may draw the respiration waveform RW illustrated in FIG. 4C and display the waveform on the display unit 5.

Note that, for convenience of explanation, the respiration rate calculation step S3 will be described below with reference to the drawn respiration waveform RW, but this does not mean that the respiration rate calculation step S3 is executed on the basis of the drawn waveform. The respiration rate calculation step S3 may be executed only on the basis of data indicating the respiration waveform RW.

Respiration Rate Calculation Step S3

In the respiration rate calculation step S3, the respiration rate calculation unit 32 calculates (estimates) the respiration rate of the subject S on the basis of the data indicating the respiration waveform RW calculated by the respiration waveform calculation unit 31.

Figure 5:
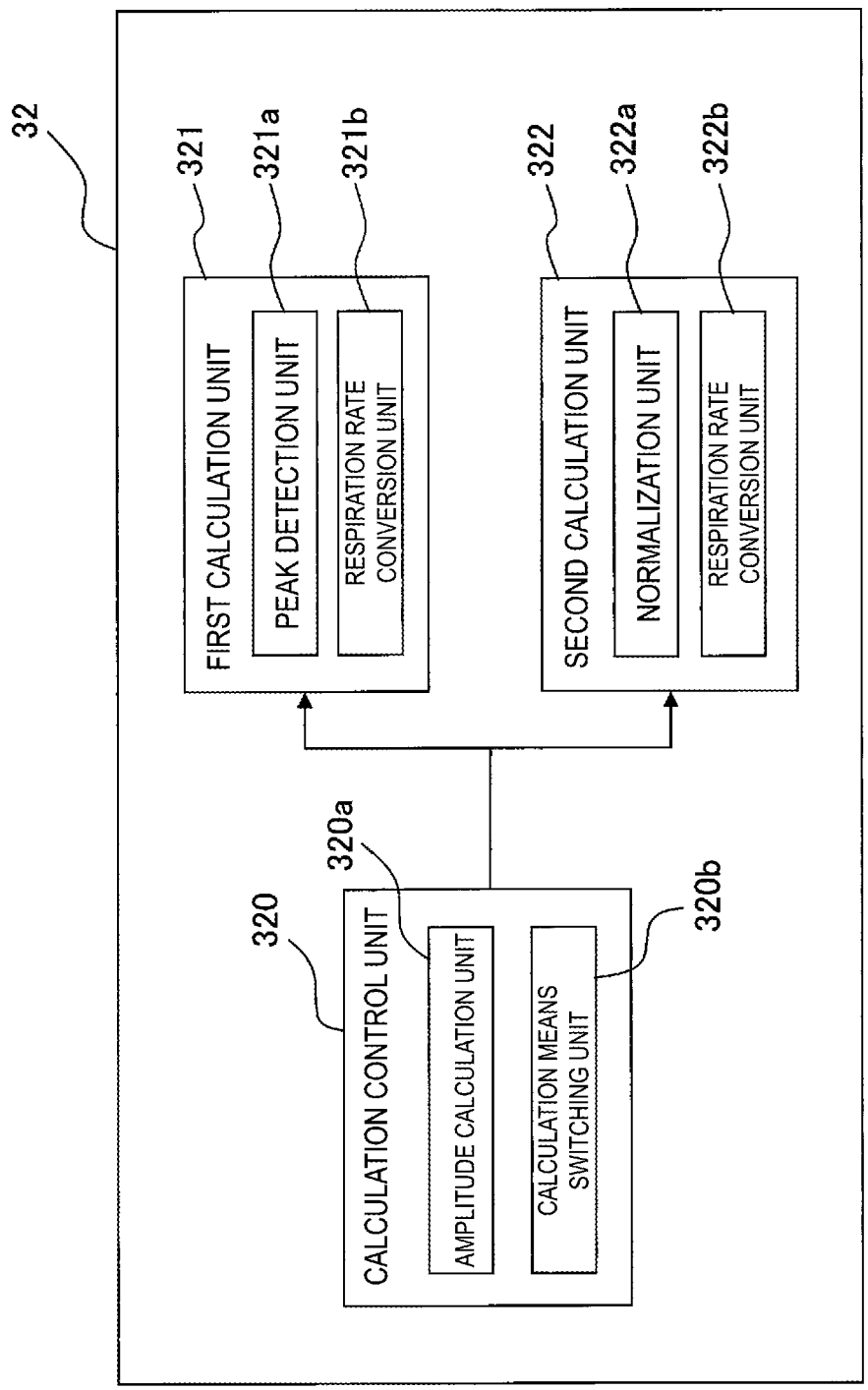
FIG. 5 is a block diagram illustrating a specific configuration of a respiration rate calculation unit.

As illustrated in FIG. 5, the respiration rate calculation unit 32 includes a calculation control unit 320, a first calculation unit 321, and a second calculation unit 322. The calculation control unit 320 includes an amplitude calculation unit 320a and a calculation means switching unit 320b. The first calculation unit 321 includes a peak detection unit 321a and a respiration rate conversion unit 321b. The second calculation unit 322 includes a normalization unit 322a and a respiration rate conversion unit 322b.

Figure 6:
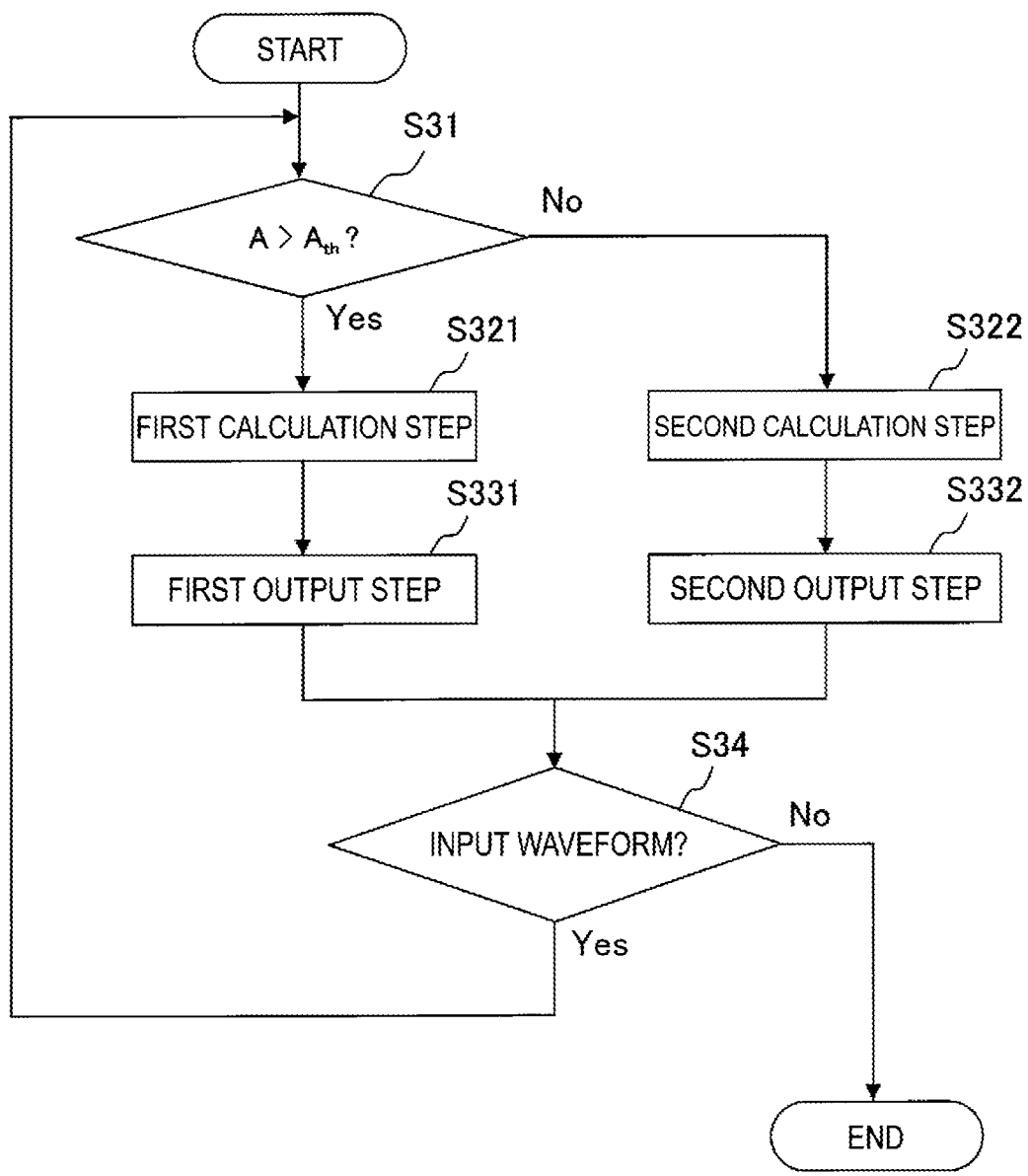
FIG. 6 is a flowchart of a procedure of a respiration rate calculation step.

As illustrated in FIG. 6, the respiration rate calculation step S3 includes an amplitude determination step S31, a first calculation step S321, a first output step S331, a second calculation step S322, a second output step S332, and a continuation determination step S34.

In the amplitude determination step S31, the calculation control unit 320 switches between causing the first calculation unit 321 to perform the first calculation step S321 and causing the second calculation unit 322 to perform the second calculation step S322 on the basis of the amplitude of the respiration waveform RW of the subject S.

Specifically, first, the amplitude calculation unit 320a of the calculation control unit 320 calculates an amplitude A of the respiration waveform RW. The amplitude calculation unit 320a is provided with a peak detection function and, as illustrated in FIG. 4C, calculates at a predetermined sampling time $t_A$ a difference between a peak of the respiration waveform RW detected immediately before calculation (here, a positive peak pp) and a peak of the respiration waveform RW detected immediately before that peak (here, a negative peak np), thereby calculating the amplitude A at the sampling time $t_A$.

Next, the calculation means switching unit 320b switches between causing the first calculation unit 321 and causing the second calculation unit 322 to calculate the respiration rate on the basis of the amplitude A calculated by the amplitude calculation unit 320a.

The calculation means switching unit 320b executes this switch on the basis of a comparison between the amplitude A of the respiration waveform RW and a predetermined threshold value $A_{th}$. Specifically, in a case in which the amplitude A is greater than the predetermined threshold value $A_{th}$, the calculation means switching unit 320b causes the first calculation unit 321 to perform the first calculation step S321 (S31: Yes). On the other hand, in a case in which the amplitude A is the predetermined threshold value $A_{th}$ or less, the calculation means switching unit 320b causes the second calculation unit 322 to perform the second calculation step S322 (No).

In the first calculation step S321 and the first output step S331, the first calculation unit 321 calculates and outputs the respiration rate of the subject S on the basis of the respiration waveform RW.

Figure 7:
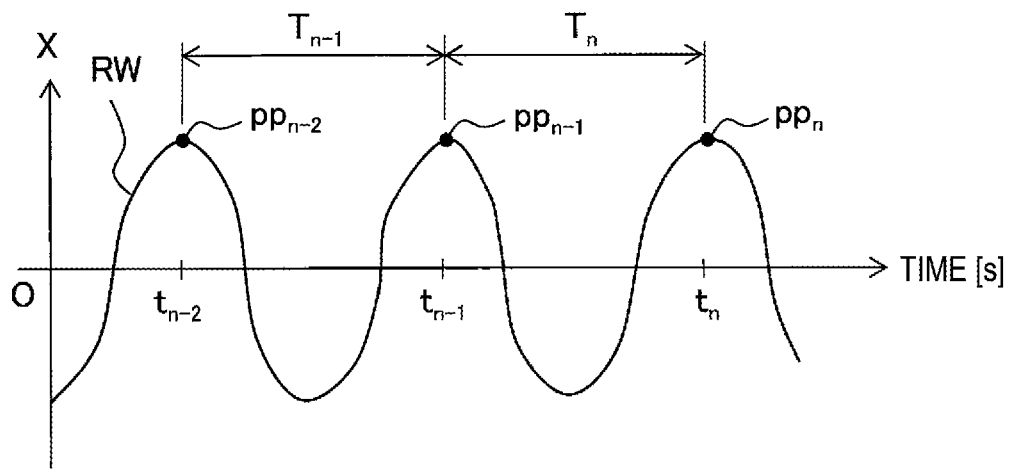
FIG. 7A is a diagram for describing calculation of a respiration rate in a first calculation unit.
FIG. 7B is a diagram for describing filtering in the first calculation unit.
Figure 7:
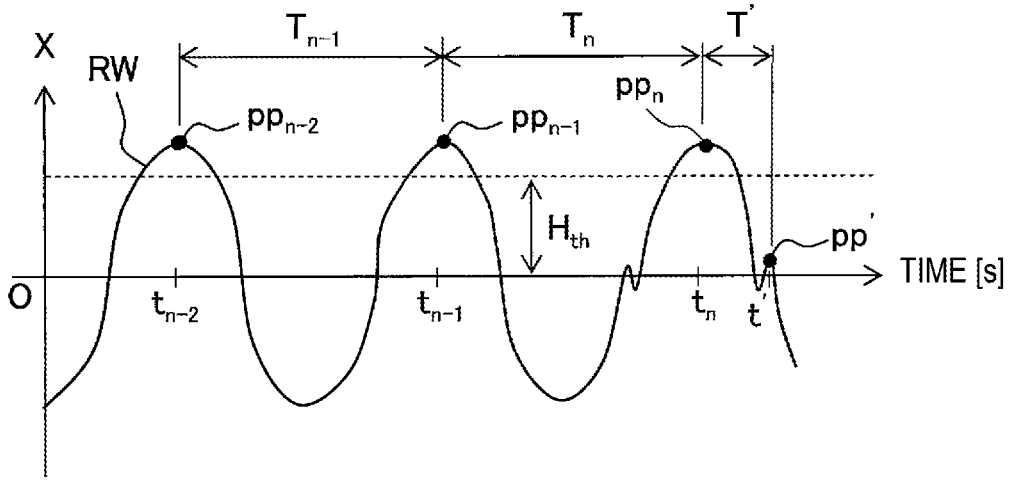

The calculation of the respiration rate by the first calculation unit 321 is performed by a first means including peak detection of the respiration waveform RW. Specifically, first, the peak detection unit 321a sequentially detects the positive peak pp (hereinafter simply referred to as "peak pp") of the respiration waveform RW. FIG. 7A illustrates peaks $pp_{n-2}$, $pp_{n-1}$, $pp_n$ of the respiration waveform RW identified by the peak detection unit 321a at times $t_{n-2}$, $t_{n-1}$, $t_n$, respectively.

Next, the respiration rate conversion unit 321b calculates a respiration rate R1 being an estimated value of the respiration rate per minute of the subject 5, on the basis of the time at which the peak of the respiration waveform RW is identified by the peak detection unit 321a. This calculation is performed as follows.

When the peak $pp_{n-1}$ is identified at time $t_{n-1}$, the respiration rate conversion unit 321b calculates an elapsed time $T_{n-1}$ between time $t_{n-1}$ and time $t_{n-2}$ at which the peak $pp_{n-2}$ was identified immediately before time $t_{n-1}$, and calculates the respiration rate R1 using Equation 1 below.

$$R1=60/T_m [\text{breaths/min}] (m=1,2,\ldots,n-1,n) \quad \text{Equation 1}$$

That is, 60 seconds is divided by the latest respiration cycle to calculate an estimated value of the respiration rate per minute that reflects the most recent respiration state. Similarly, when the peak $pp_n$ is identified at time $t_n$, the respiration rate conversion unit 321b calculates an elapsed time $T_n$ between time $t_n$ and time $t_{n-1}$ at which the peak $pp_{n-1}$ was identified immediately before time $t_n$, and calculates the respiration rate R1 using equation 1. The calculated respiration rate R1 is output to the control unit 3 (first output step S331).

Here, the peak detection unit 321a of the first calculation unit 321 is configured to adjust sensitivity at the time the peak of the respiration waveform RW is detected, and to not detect the peak for a waveform with a small amplitude. This is due to the following reasons.

The respiration waveform RW of the subject S may include noise as illustrated in FIG. 7B, and a peak pp' of the waveform corresponding to the noise occurs independent of the respiration cycle of the subject S. Therefore, if the peak detection unit 321a detects up to the peak pp' of the waveform corresponding to the noise, the respiration rate conversion unit 321b calculates the respiration rate R1 independent of the respiration cycle of the subject S, thereby reducing the reliability of the calculated respiration rate R1.

Specifically, as illustrated in FIG. 7B, in a case in which the peak detection unit 321a detects the peak pp' due to noise at a time t' immediately after the time $t_n$, the respiration rate conversion unit 321b calculates the respiration rate R1 using an elapsed time T' from time $t_n$ to time t' (Equation 1). In this case, because the elapsed time T' is a small value independent of the respiration cycle of the subject S, the calculated value of the respiration rate R1 is a large value that does not reflect the respiration condition of the subject S.

In contrast, the peak detection unit 321a of the first calculation unit 321 according to the present embodiment is configured to not detect a peak of a waveform lower than a predetermined height $H_{th}$ (FIG. 7B) by filtering. This suppresses the effect of noise, and ensures that only peaks corresponding to the respiration of the subject S are accurately detected.

In the second calculation step S322 and the second output step S332, the second calculation unit 322 calculates and outputs the respiration rate of the subject S on the basis of the respiration waveform RW.

The calculation of the respiration rate by the second calculation unit 322 is performed by a second means including normalization of the respiration waveform RW. Specifically, first, the normalization unit 322a of the second calculation unit 322 normalizes the respiration waveform RW (top half of FIG. 8). Normalization is performed using Equation 2 below.

$$Y = X/(\alpha + |X|) \quad (0 < \alpha < 1) \quad \text{Equation 2}$$

Figure 8:
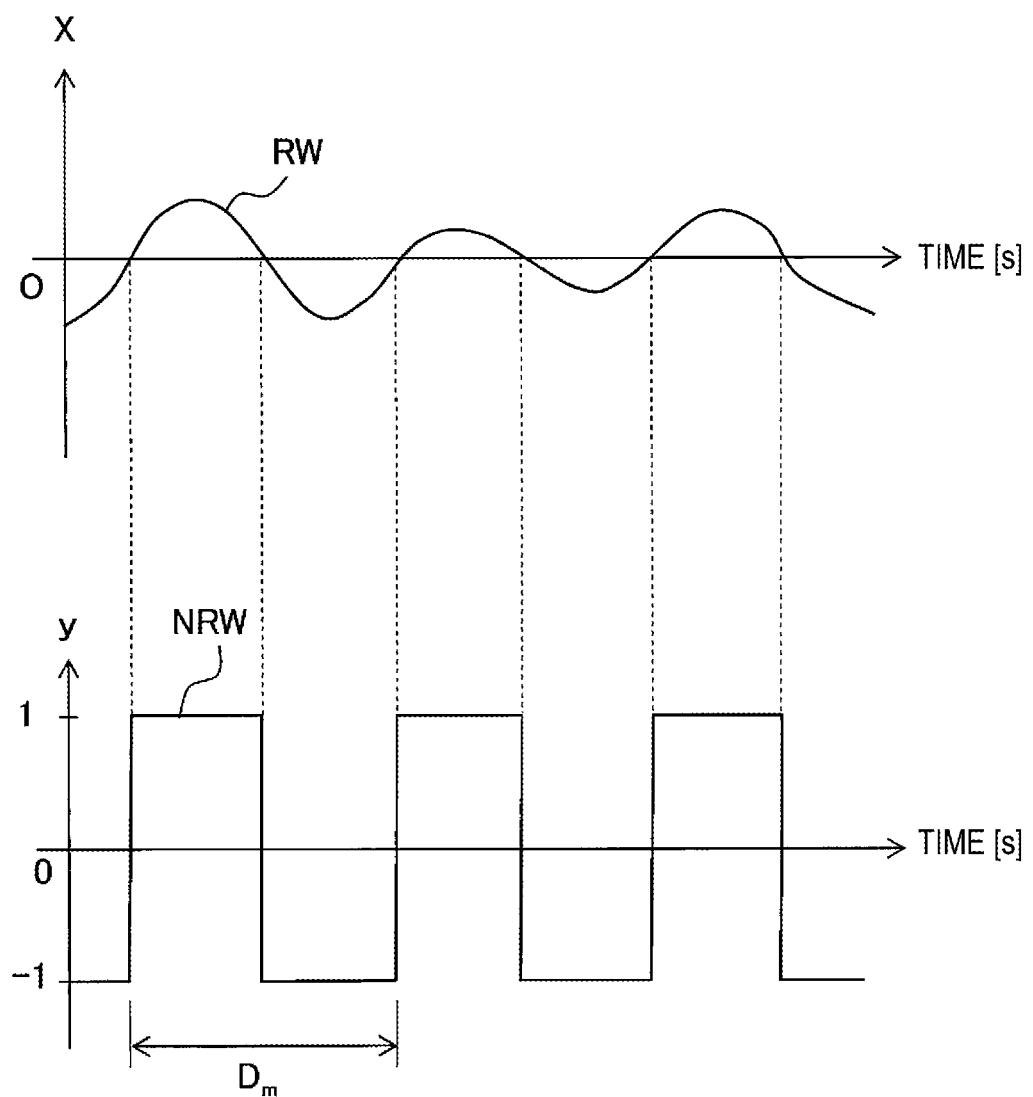
FIG. 8 is a diagram for describing the calculation of the respiration rate in a second calculation unit.

In Equation 2, "X" is the distance X described above and "α" is a constant. When the value of α is close to 0, the shape of a normalized respiration waveform NRW acquired by normalization (bottom half of FIG. 8) is close to a rectangular wave. When the value of α is close to 1, the shape of the normalized respiration waveform NRW acquired by normalization is close to the shape of the respiration waveform RW before normalization. The respiration waveform NRW illustrated in the bottom half of FIG. 8 is a waveform calculated with $\alpha \approx 0$.

Next, the respiration rate conversion unit 322b calculates a respiration rate R2 being an estimated value of the respiration rate per minute of the subject S, on the basis of an inter-pulse distance Dm of the normalized respiration waveform NRW. In the lower half of FIG. 8, the distance between the rising of the pulses is defined as the inter-pulse distance Dm, but the distance between the falling of the pulses may be the inter-pulse distance Dm. The calculation of the respiration rate R2 by the respiration rate conversion unit 322b is performed using the equation below (Equation 3).

$$R2 = 60/D_m \text{ [breaths/min]} \quad (m = 1, 2, \ldots, n-1, n) \quad \text{Equation 3}$$

That is, 60 seconds is divided by the latest inter-pulse distance to calculate an estimated value of the respiration rate per minute that reflects the most recent respiration state, and this value is the respiration rate R2. The calculated respiration rate R2 is output to the control unit 3 (second output step S332).

The respiration rate R2 is calculated after the effects of the amplitude A of the respiration waveform RW have been removed by normalization. Therefore, the respiration rate R2 can be calculated accurately even in a case in which the respiration of the subject is weak and fluctuates erratically, causing the amplitude A of the respiration waveform RW to be small and fluctuating.

After the first output step S331 or the second output step S332, the respiration rate calculation unit 32 performs the continuation determination step S34 and, in a case in which there is continuous input of the respiration waveform RW, subsequently performs the amplitude determination step S31.

A specific example of respiration rate calculation by the respiration rate calculation unit 32 will be described with reference to FIG. 9.

Figure 9:
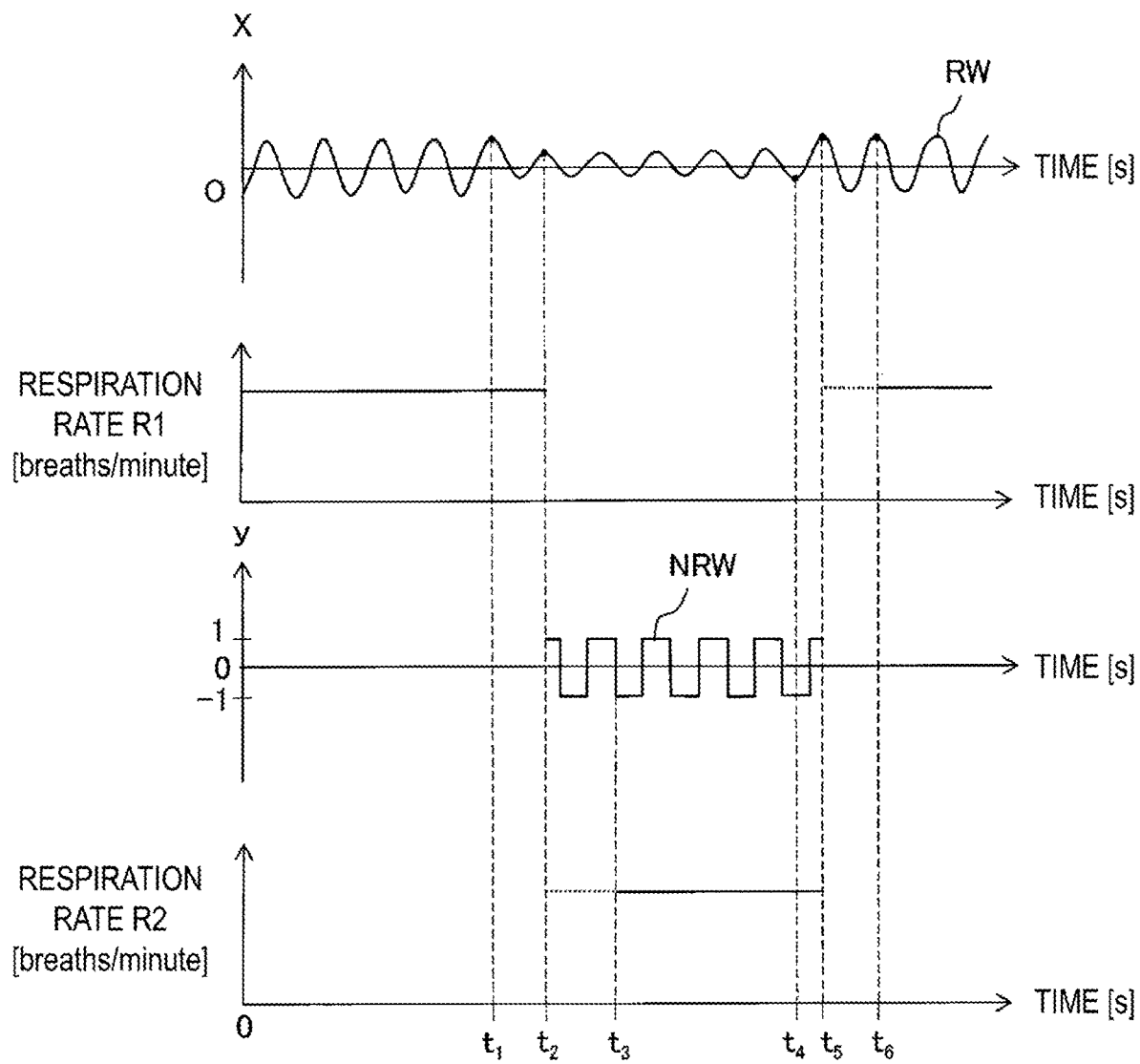
FIG. 9 is a diagram illustrating a specific example of the respiration rate calculation step performed by the respiration rate calculation unit.

First, in the periods up to time $t_1$ and after time $t_5$ in FIG. 9, the subject S maintains a normal respiration state and the respiration waveform RW oscillates at an amplitude of a predetermined value or greater. On the other hand, in the period from time $t_2$ to time $t_4$, the subject S is in a weak respiration state and the amplitude of the respiration waveform RW is reduced. Such weakening of respiration can occur, for example, in a case in which the condition of a subject under terminal care (end-of-life care) worsens, or when a patient with sleep apnea syndrome (SAS) sleeps.

In the period up to time $t_1$, the calculation control unit 320 determines that the amplitude A of the respiration waveform RW is the threshold value $A_{th}$ or greater and causes the first calculation unit 321 to calculate and output the respiration rate R1. The output respiration rate R1 is illustrated in the second graph of FIG. 9.

Next, when time $t_2$ is reached, the calculation control unit 320 determines that the amplitude A of the respiration waveform RW is the threshold value $A_{th}$ or less and causes the second calculation unit 322 to calculate and output the respiration rate R2. The normalized respiration waveform NRW calculated by the normalization unit 322a of the second calculation unit 322 is calculated on the basis of the calculation by the respiration rate conversion unit 322b in the third graph of FIG. 9, and the output respiration rate R2 is illustrated in the fourth graph.

Note that, after the calculation of the respiration rate R2 by the second calculation unit 322 is started at time $t_2$, the respiration rate conversion unit 322b cannot calculate the respiration rate R2 using Equation 3 until the initial inter-pulse distance $D_m$ is calculated at time $t_3$. Accordingly, for this period, the respiration rate R1 calculated at the time of time $t_2$ may be used as a preliminary respiration rate.

Next, when time $t_5$ is reached, the calculation control unit 320 determines that the amplitude A of the respiration waveform RW is greater than the threshold value $A_{th}$ and causes the first calculation unit to calculate and output the respiration rate R1.

Note that, after the calculation of the respiration rate R1 by the first calculation unit 321 is started at time $t_5$, the first calculation unit 321 cannot calculate the respiration rate using Equation 1 until the next peak is detected at time to. Accordingly, for this period, the respiration rate R2 calculated at the time of time $t_5$ may be used as a preliminary respiration rate.

In this manner, the respiration rate calculation unit 32, in a case in which the subject S breathes normally and the amplitude A of the respiration waveform RW has sufficient magnitude, calculates, by the first calculation unit 321, the respiration rate R1 having the effects of noise removed by sensitivity adjustment, and in a case in which the breathing of the subject S weakens and the amplitude A of the breathing waveform RW does not have a sufficient magnitude, calculates, by the second calculation unit 322, the respiration rate R2 having the effects of the amplitude A of the respiration waveform RW removed by normalization. That is, the respiration rate calculation unit 32, in a case in which the subject S is breathing normally, accurately calculates (estimates) the respiration rate of the subject S using calculation means suitable for normal breathing and, in a case in which the breathing of the subject S weakens, switches to calculation means suitable for weak breathing to maintain accurate calculation (estimation) of the respiration rate of the subject S.

Bed Occupancy Determination Step

In the bed occupancy determination step S4, the bed occupancy determination unit 33 determines whether or not the subject S occupies the bed BD.

This determination is made on the basis of the respiration rates R1, R2 of the subject S. Specifically, for example, the bed occupancy determination unit 33 determines that the subject S does not occupy the bed BD, that is, is in an "out-of-bed state" when the respiration rate R1 and respiration rate R2 of the subject S have not been measured.

Further, the bed occupancy determination unit 33 determines that the subject S is in an "out-of-bed state" when the calculated respiration rates R1, R2 are outside a predetermined range (from 5 breaths to 30 breaths, for example). A person takes approximately 12 to 20 breaths per minute. Therefore, in a case in which the calculated respiration rates R1, R2 significantly deviate from this range, the calculated values conceivably do not correspond to the respiration of the subject S and are caused by some disturbance.

On the other hand, in a case in which the respiration rate R1 or the respiration rate R2 has been calculated and the value of the calculated respiration rate R1 or respiration rate R2 is within the predetermined range, the bed occupancy determination unit 33 determines that the subject S occupies the bed BD, that is, is in an "in-bed state".

Subsequently, the bed occupancy determination unit 33 outputs the determination result to the control unit 3.

Display Step

In the display step S5, the control unit 3 displays, on the display unit 5, the respiration rate of the subject S and whether or not the subject S is in an "in-bed state" or an "out-of-bed state" on the basis of the outputs from the first calculation unit 321, the second calculation unit 322, and the bed occupancy determination unit 33.

Further, in the display step S5, in addition to or in lieu of the display using the display unit 5, a notification may be made using the notification unit 6. In this case, for example, when the subject S moves, a notification sound is generated, notifying a nurse, a caregiver, or the like who is the user of the biological information monitoring system 100 of the occurrence of body movement.

The effects of the biological information monitoring system 100 of this embodiment are summarized below.

The physiological state monitoring system 100 of this embodiment includes the respiration rate calculation unit 32 configured to calculate the respiration rate R2 by normalizing the respiration waveform RW in a case in which the breathing of the subject S weakens and the amplitude A of the respiration waveform RW decreases. Accordingly, even in a case in which the breathing of the subject S weakens and the amplitude A of the respiration waveform RW decreases or becomes unstable, the effects of the amplitude A are removed by normalization, making it possible to calculate (estimate) the correct respiration rate. That is, biological information of the subject can be calculated more accurately.

In a case in which the subject S breaths normally and the amplitude A of the respiration waveform RW has a sufficient magnitude, the respiration rate calculation unit 32 included in the physiological state monitoring system 100 of this embodiment is configured to calculate the respiration rate R1 having the effects of noise included in the respiration waveform RW removed on the basis of peak detection. Therefore, in a case in which the subject S breaths normally, the physiological state monitoring system 100 of the present embodiment can calculate (estimate) the respiration rate more accurately.

That is, the physiological state monitoring system 100 according to this embodiment is configured to, in a case in which the breathing of the subject weakens and respiration rate calculation based on the peak detection cannot be performed, perform respiration rate calculation based on normalization to reliably and accurately calculate the respiration rate and, in a case in which the subject is breathing normally, perform respiration rate calculation based on peak detection to calculate the respiration rate with higher accuracy.

The biological information monitoring system 100 of this embodiment can determine the bed occupancy of the subject S with high accuracy on the basis of the respiration rate of the subject S calculated with high accuracy by the respiration rate calculation unit 32.

The body movement determination system of this embodiment and the biological information monitoring system 100 including this system monitor the physiological state of the subject S by using the load detectors 11 to 14 disposed below the legs $BL_1$ to $BL_4$ of the bed BD, respectively. Accordingly, there is no need to attach a measurement device to the body of the subject S, and the subject S is not subjected to discomfort or an unpleasant sensation.

Modifications

In the biological information monitoring system 100 of the above-described embodiment, the following modifications may also be employed.

In the biological information monitoring system 100 of the above-described embodiment, the respiration waveform calculation unit 31 may be configured as a waveform calculation unit that calculates, in addition to the respiration waveform RW, a waveform indicating a load fluctuation in accordance with a heartbeat of the subject S, and the respiration rate calculation unit 32 may be configured as a biological information calculation unit that also calculates the heart rate of the subject.

In this modification, the waveform calculation unit separates components included in a frequency band of the heartbeat (from approximately 0.5 Hz to approximately 3.3 Hz) from at least one of the load signals $s_1$ to $s_4$ by a bandpass filter or the like, and transmits the components to the biological information calculation unit as a waveform indicating the load fluctuation in accordance with the heartbeat of the subject S.

The biological information calculation unit calculates the heart rate of the subject S by the same step as the respiration rate calculation step S3 of the embodiment described above. The waveform indicating the load fluctuation in accordance with the heartbeat of the subject S is also a waveform of a time domain similar to that of the respiration waveform RW, and therefore the biological information calculation unit can apply a process equivalent to the process performed by the respiration rate calculation unit 32 of the above-described embodiment on the respiration waveform RW to the waveform indicating the load fluctuation in accordance with the heartbeat of the subject S, and calculate the heart rate of the subject S with high accuracy.

Note that the waveform calculation unit may be configured as a waveform calculation unit that only calculates the waveform indicating the load fluctuation in accordance with the heartbeat of the subject S, and the biological information calculation unit may be configured as a biological information calculation unit that only calculates the heart rate of the subject.

In the biological information monitoring system 100 of the above-described embodiment, the respiration waveform calculation unit 31 may calculate a waveform obtained by separating components included in the respiration frequency band (from approximately 0.2 Hz to approximately 0.33 Hz) from at least one of the load signals $s_1$ to $s_4$, and transmit that waveform instead of the respiration waveform RW to the respiration rate calculation unit 32. The waveform obtained by separating the components included in the respiration frequency band from at least one of the load signals $s_1$ to $s_4$ is also a waveform in the same time domain as that of the respiratory waveform RW, and therefore the respiratory waveform calculation unit 32 can calculate the respiration rate of the subject S with high accuracy by a process equivalent to the process performed on the respiratory waveform RW in the above-described embodiment.

The respiration waveform and the waveform obtained by separating the components included in the respiration frequency band from at least one of the load signals $s_1$ to $s_4$ are examples of a "waveform indicating a temporal variation in a detected value of a load detector in accordance with respiration of the subject" described in the claims, and the waveform obtained by separating the components included in the heartbeat frequency band from at least one of the load signals $s_1$ to $s_4$ is an example of a "waveform indicating a temporal variation in a detected value of a load detector in accordance with a heartbeat of the subject" described in the claims.

In the above-described embodiment, the calculation control unit 320 of the respiration rate calculation unit 32 may include a biological signal determination unit (not illustrated) configured to determine whether or not the amplitude A calculated by the amplitude calculation unit 320a is based on the respiration of the subject S. The biological signal determination unit is configured to determine whether or not the calculated amplitude A is based on the respiration, that is, the biological signal, of the subject S using, as a standard, the regularity, randomness, or the like of the respiration waveform. In a mode in which the biological signal determination unit is provided, a case in which a small value is calculated as the amplitude A due to the effects of noise on the respiration waveform RW (FIG. 7B), causing a switch to calculation by the second calculation unit 322, is suppressed.

In the biological information monitoring system 100 of the above-described embodiment, the first calculation unit 321 may calculate the respiration rate R1 on the basis of the identification of the negative peak np instead of the positive peak pp. The specific steps in this case are the same as those of the above-described embodiment.

In the biological information monitoring system 100 of the above-described embodiment, the first calculation unit 321 may calculate the respiration rate R1 by means different from peak detection. Specifically, for example, frequency analysis can be applied to the respiration waveform RW calculated for a period (about 60 seconds, for example) from the time of calculation to find the peak frequency, and an estimated value of the respiration rate of the subject S can be calculated on the basis of the found peak frequency. Specifically, for example, if the peak frequency of the respiration waveform RW is 0.3 Hz, the respiration rate of the subject S can be calculated as 0.3 breaths per second and 18 breaths per minute. Alternatively, the rise count or fall count per minute can be calculated (estimated) from a zero-cross rise count or fall count of the respiration waveform RW, and the acquired value can be an average respiration rate of the subject S per minute. Specifically, for example, if the zero-cross rise count of the respiration waveform RW occurring in a 15-second period is four, then 16 breaths, which is four times that amount, can be estimated as the average respiration rate per minute of the subject S. In addition, the first calculation unit 321 may calculate the respiration rate of the subject S using various means.

In the biological information monitoring system 100 of the above-described embodiment, the second calculation unit 322 can normalize the respiration waveform RW without using Equation 2. Specifically, for example, the respiratory waveform RW can be normalized by using a sigmoid function or a hyperbolic tangent instead of Equation 2.

In the biological information monitoring system 100 of the above-described embodiment, the bed occupancy determination unit 33 may determine whether the subject is in an "in-bed state" or an "out-of-bed state" on the basis of the heart rate of the subject or on the basis of the respiration rate and the heart rate of the subject. Bed occupancy determination based on the heart rate of the subject can be performed on the basis of whether or not a heart rate calculation has been made and/or whether or not the calculated heart rate is within a predetermined range corresponding to that of a human heartbeat, or the like, similarly to the bed occupancy determination based on the respiration rate of the subject.

The biological information monitoring system 100 of the above-described embodiment may further include a physiological state determination unit configured to determine the presence or absence of body movement of the subject S and various physiological states of the subject S. Such a physiological state determination unit is configured to perform an asleep/awake determination, viability determination, and the like of the subject S on the basis of the respiration rate of the subject S, for example.

The biological information monitoring system 100 of the above-described embodiment need not necessarily include all of the load detectors 11 to 14, and may only be provided with any one of these. Further, the load detectors need not necessarily be disposed at the four corners of the bed and can be disposed at any position so as to be able to detect the load and variations of the load of the subject on the bed. Further, each of the load detectors 11 to 14 is not limited to being a load sensor that uses a beam type load cell, and, for example, a force sensor can be used.

Figure 10:
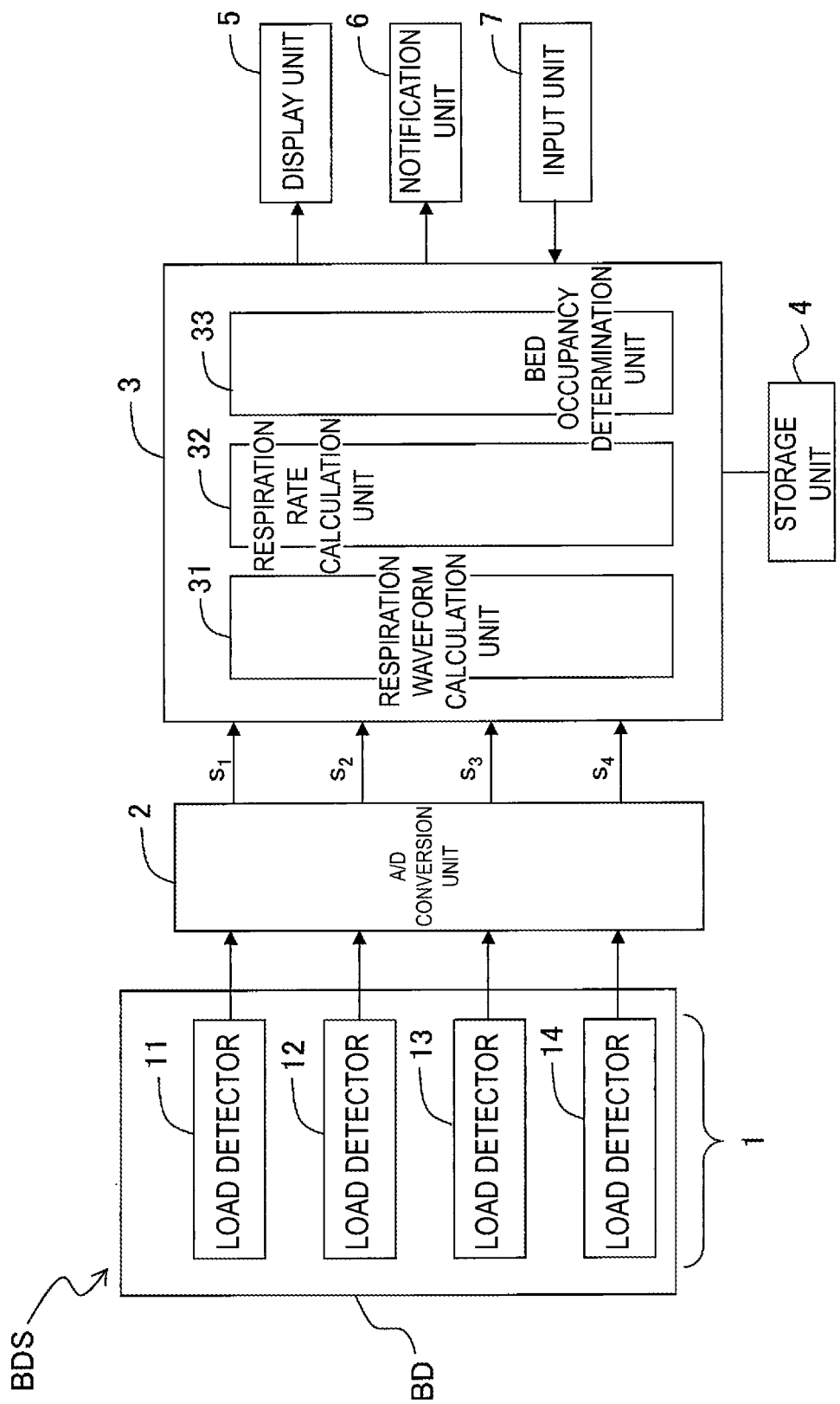
FIG. 10 is a block diagram illustrating an overall configuration of a bed system according to a modified example.

In the biological information monitoring system 100 of the above-described embodiment, each of the load detectors 11 to 14 is disposed below a caster C attached to the lower end of the leg of the bed BD, but is not limited this location. The load detectors 11 to 14 may be respectively provided between the four legs of the bed BD and a bed board of the bed BD or, if the four legs of the bed BD can be vertically separated, may be provided between upper legs and lower legs. Further, the load detector 11 to 14 may also be integrally or detachably combined with the bed BD to configure a bed system BDS consisting of the bed BD and the body movement determination system or the biological information monitoring system 100 of this embodiment (FIG. 10). Note that, in the present specification, a load detector provided at the bed refers to a load detector provided between the four legs of the bed BD and the bed board of the bed BD and a load detector provided between the upper leg and the lower leg, as described above.

In the biological information monitoring system 100 of the above-described embodiment, a signal amplification unit configured to amplify the load signal from the load detection unit 1, and a filtering unit configured to remove noise from the load signal may be provided between the load detection unit 1 and the A/D conversion unit 2.

In the biological information monitoring system 100 of the above-described embodiment, the display unit 5 may include a simple visual display means, such as a printer for printing and outputting information indicating biological information, a light for displaying biological information, or the like instead of or in addition to the monitor. The notification unit 6 may be provided with a vibration generation unit configured to carry out notification by vibration instead of or in addition to the speaker.

As long as the features of the present invention are maintained, the present invention is not limited to the embodiments described above, and other focus considered within the scope of the technical concept of the present invention are also included within the scope of the present invention.

INDUSTRIAL APPLICABILITY

According to the biological information monitoring system of the present invention, biological information such as a respiration rate of a subject can be calculated with high accuracy, making it possible to improve the quality of medical and long-term care and the like.

REFERENCE SIGNS LIST

1 Load detection unit
11, 12, 13, 14 Load detector
2 A/D conversion unit
3 Control unit
31 Respiration waveform calculation unit
32 Respiration rate calculation unit
33 Bed occupancy determination unit
320 Calculation control unit
321 First calculation unit
322 Second calculation unit
4 Storage unit
5 Display unit
6 Notification unit
7 Input unit
100 Biological information monitoring system
BD Bed
BDS Bed system
S Subject

The invention claimed is:

1. A biological information monitoring system configured to monitor biological information of a subject on a bed, the biological information monitoring system comprising:
at least one load detector provided below the bed or legs of the bed and configured to detect a load of the subject on the bed; and
a controller configured to:
calculate a waveform indicating a temporal variation in a detected value of the at least one load detector in accordance with respiration or a heartbeat of the subject; and
calculate a respiration rate or a heart rate of the subject by using the waveform,
the calculating of the respiration rate or the heart rate of the subject including
calculating the respiration rate or the heart rate of the subject by a first means based on the waveform, and
calculating the respiration rate or the heart rate of the subject by a second means that differs from the first means and includes normalizing the waveform, and
the controller is further configured to calculate the respiration rate or the heart rate by the second means when an amplitude of the waveform is a threshold value or less.

2. The biological information monitoring system according to claim 1, wherein
the at least one load detector is a plurality of load detectors,
the controller is configured to find a center of gravity position of the subject based on a detected value of each of the plurality of load detectors, and calculate a respiration waveform of the subject based on movement of the center of gravity position in accordance with the respiration of the subject,
the controller is configured to calculate the respiration rate of the subject by the first means based on the respiration waveform,
the controller is configured to calculate the respiration rate of the subject by the second means that includes normalizing the respiration waveform, and
the controller is configured to calculate the respiration rate by the second means that includes normalizing the respiration waveform when an amplitude of the respiration waveform is the threshold value or less.

3. The biological information monitoring system according to claim 1, wherein the first means includes detecting a peak of the waveform.

4. The biological information monitoring system according to claim 1, wherein the controller is further configured to determine whether or not the subject occupies the bed based on the respiration rate or the heart rate of the subject being calculated.

5. The biological information monitoring system according to claim 1, wherein
the controller is configured to calculate the waveform indicating the temporal variation in the detected value of the at least one load detector in accordance with the respiration of the subject, and the waveform indicating the temporal variation in the detected value of the at least one load detector in accordance with the heartbeat of the subject,
the controller is configured to calculate the respiration rate of the subject by the first means based on the waveform indicating the temporal variation in accordance with the respiration, and calculate the heart rate of the subject by the first means based on the waveform indicating the temporal variation in accordance with the heartbeat,
the controller is configured to calculate the respiration rate of the subject by the second means that includes normalizing the waveform indicating the temporal variation in accordance with the respiration, and calculate the heart rate of the subject by the second means that includes normalizing the waveform indicating the temporal variation in accordance with the heartbeat, and
the controller is configured to calculate the respiration rate by the second means that includes normalizing the waveform indicating the temporal variation in accordance with the respiration when an amplitude of the waveform indicating the temporal variation in accordance with the respiration is a first threshold value or less, and calculate the heart rate by the second means that includes normalizing the waveform indicating the temporal variation in accordance with the heartbeat when an amplitude of the waveform indicating the temporal variation in accordance with the heartbeat is a second threshold value or less.

6. A bed system comprising:
a bed; and
the biological information monitoring system according to claim 1.

7. A biological information monitoring method for monitoring biological information of a subject on a bed, the method comprising:
detecting a load of the subject on the bed by at least one load detector provided below the bed or legs of the bed;
calculating a waveform indicating a temporal variation in a detected value of the at least one load detector in accordance with respiration or a heartbeat of the subject; and calculating a respiration rate or a heart rate of the subject by using the waveform, the calculating the respiration rate or the heart rate of the subject including calculating the respiration rate or the heart rate of the subject by a first means based on the waveform, calculating the respiration rate or the heart rate of the subject by a second means that differs from the first means and includes normalizing the waveform, and performing the calculating of the respiration rate or the heart rate by the second means when an amplitude of the waveform is a threshold value or less.

8. The biological information monitoring method according to claim 7, wherein the at least one load detector is a plurality of load detectors, the calculating a waveform includes finding a center of gravity position of the subject based on a detected value of each of the plurality of load detectors, and calculating a respiration waveform of the subject based on movement of the center of gravity position in accordance with the respiration of the subject, the calculating the respiration rate of the subject by the first means includes calculating the respiration rate of the subject by the first means based on the respiration waveform, the calculating the respiration rate of the subject by the second means includes calculating the respiration rate of the subject by the second means that includes normalizing the respiration waveform, and the performing of the calculating of the respiration rate by the second means when an amplitude of the waveform is a threshold value or less includes performing the calculating of the respiration rate by the second means that includes normalizing the respiration waveform when an amplitude of the respiration waveform is the threshold value or less.

9. The biological information monitoring method according to claim 7, wherein the first means includes detecting a peak of the waveform.

10. The biological information monitoring method according to claim 7, further comprising determining whether or not the subject occupies the bed based on the respiration rate or the heart rate of the subject being calculated.

11. The biological information monitoring method according to claim 7, wherein the calculating a waveform indicating a temporal variation in a detected value of the at least one load detector in accordance with respiration or a heartbeat of the subject includes calculating the waveform indicating the temporal variation in the detected value of the at least one load detector in accordance with the respiration of the subject, and further includes calculating the waveform indicating the temporal variation in the detected value of the at least one load detector in accordance with the heartbeat of the subject, the calculating a respiration rate or a heart rate of the subject by using the waveform includes calculating the respiration rate of the subject by using the waveform indicating the temporal variation in the detected value of the at least one load detector in accordance with the respiration of the subject, and further includes calculating the heart rate of the subject by using the waveform indicating the temporal change in the detected value of the at least one detector in accordance with the heartbeat of the subject, and the calculating the respiration rate and the heart rate of the subject includes calculating the respiration rate of the subject by the first means based on the waveform indicating temporal variation in accordance with the respiration of the subject, calculating the heart rate of the subject by the first means based on the waveform indicating temporal variation in accordance with the heartbeat of the subject, calculating the respiration rate of the subject by the second means that includes normalizing the waveform indicating temporal variation in accordance with the respiration of the subject, calculating the heart rate of the subject by the second means that includes normalizing the waveform indicating temporal variation in accordance with the heartbeat of the subject, performing the calculating of the respiration rate by the second means that includes normalizing the waveform indicating temporal variation in accordance with the respiration of the subject when an amplitude of the waveform indicating temporal variation in accordance with the respiration of the subject is a first threshold value or less, and performing the calculating of the heart rate by the second means that includes normalizing the waveform indicating temporal variation in accordance with the heartbeat of the subject when an amplitude of the waveform indicating temporal variation in accordance with the heartbeat of the subject is a second threshold value or less.

* * * * *